(12) United States Patent
Jakubowski et al.

(10) Patent No.: US 6,943,146 B2
(45) Date of Patent: Sep. 13, 2005

(54) METHOD FOR PROMOTING NEOVASCULARIZATION

(75) Inventors: Aniela Jakubowski, Arlington, MA (US); Linda Burkly, West Newton, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 10/275,997

(22) PCT Filed: May 7, 2001

(86) PCT No.: PCT/US01/14545
§ 371 (c)(1), (2), (4) Date: Nov. 8, 2002

(87) PCT Pub. No.: WO01/85193
PCT Pub. Date: Nov. 15, 2001

(65) Prior Publication Data
US 2003/0211993 A1 Nov. 13, 2003

Related U.S. Application Data
(60) Provisional application No. 60/202,738, filed on May 8, 2000.

(51) Int. Cl.[7] .............................................. A61K 38/18
(52) U.S. Cl. ........................ 514/12; 530/350; 424/1.41
(58) Field of Search ...................... 930/140; 530/350; 514/2, 12; 424/1.41

(56) References Cited

U.S. PATENT DOCUMENTS

| | | |
|---|---|---|
| 5,073,492 A | 12/1991 | Chen et al. |
| 5,858,991 A | 1/1999 | Hellerqvist et al. |
| 6,207,642 B1 | 3/2001 | Wiley |
| 6,448,042 B1 | 9/2002 | Greene et al. |
| 6,544,761 B2 * | 4/2003 | Greene et al. ............. 435/69.2 |
| 6,727,225 B2 | 4/2004 | Wiley |

(Continued)

FOREIGN PATENT DOCUMENTS

| | | |
|---|---|---|
| WO | WO 96/18725 | 6/1996 |
| WO | WO 98/05783 | 2/1998 |
| WO | WO 98/35061 | 8/1998 |
| WO | WO 98/55508 | 12/1998 |
| WO | WO 99/11791 | 3/1999 |
| WO | WO 99/19490 | 4/1999 |
| WO | WO 99/59614 | 11/1999 |
| WO | WO 99/61471 | 12/1999 |
| WO | WO 00/37638 | 6/2000 |
| WO | WO 00/42073 | 7/2000 |
| WO | WO 01/45730 | 6/2001 |
| WO | WO 01/53486 | 7/2001 |
| WO | WO 03/086311 | 10/2003 |

OTHER PUBLICATIONS

Lynch, C. N. et al., "TWEAK Induces Angiogenesis and Proliferation of Endothelial Cells," *Journal of Biological Chemistry* 274(13): 8455–8459 (1999).

Jakubowski, A. et al., "TWEAK Synergizes With Basic Fibroblast Growth Factor to Induce Endothelial Cell Proliferation, Migration and Lumen Morphogenesis," *Scandinavian Journal of Immunology* 51(Supplement 1): 62 (2000).

U.S. Appl. No. 09/245,198, Chicheportiche et al.

U.S. Appl. No. 10/978,203, Chicheportiche et al.

U.S. Appl. No. 10/978,131, Chicheportiche et al.

(Continued)

*Primary Examiner*—Robert A. Wax
(74) *Attorney, Agent, or Firm*—Fish & Richardson P.C.

(57) ABSTRACT

The present invention relates to a method for enhancing angiogenic activity to promote neovascularization comprising administering to a subject a formulation comprising a synergistically effective amount of a TWEAK agonist and an angiogenic factor.

9 Claims, 4 Drawing Sheets

Effect of Tweak on endothelial cells proliferation. HUVEC were cultured for 3-4 days in basal media supplemented with Tweak in the presence or absence of bFGF and pulsed with $^3$H-Thy for the last 18 hours. Anti-Tweak mAb (10ug/ml) blocks Tweak (100ng/ml) enhancing effect on bFGF (1/500 dilution)

U.S. PATENT DOCUMENTS

| | | |
|---|---|---|
| 6,824,773 B2 | 11/2004 | Wiley |
| 2002/0004041 A1 | 1/2002 | Albert et al. |
| 2002/0041876 A1 | 4/2002 | Wiley |
| 2002/0042368 A1 | 4/2002 | Fanslow, III et al. |
| 2002/0110853 A1 | 8/2002 | Wiley |
| 2003/0100074 A1 | 5/2003 | Yu et al. |
| 2003/0162712 A1 | 8/2003 | Cerretti et al. |
| 2003/0170228 A1 | 9/2003 | Ashkenazi et al. |
| 2003/0198640 A1 | 10/2003 | Yu et al. |
| 2003/0211096 A1 | 11/2003 | Ashkenazi et al. |
| 2003/0216546 A1 | 11/2003 | Tykocinski et al. |
| 2004/0014176 A1 | 1/2004 | Ashkenzai et al. |
| 2004/0018170 A1 | 1/2004 | Shirwan |
| 2004/0033225 A1 | 2/2004 | Browning et al. |
| 2004/0038349 A1 | 2/2004 | Hilbert et al. |
| 2004/0047854 A1 | 3/2004 | Black et al. |
| 2004/0091473 A1 | 5/2004 | DuBose et al. |
| 2005/0008636 A1 | 1/2005 | Rennert |
| 2005/0054568 A1 | 3/2005 | Ling et al. |

OTHER PUBLICATIONS

Chicheportiche et al. "Down–regulated expression of TWEAK mRNA in acute and chronic inflammatory Pathologies." Biochem Biophys Res Commun. Dec. 9, 2000;279(1):162–5.

Chicheportiche et al. "Proinflammatory activity of TWEAK on human dermal fibroblasts and synoviocytes: blocking and enhancing effects of anti–TWEAK monoclonal antibodies." Arthritis Res. 2002;4(2):162–33. Epub Nov. 9, 2001.

Chicheportiche et al. "TWEAK, a new secreted ligand in the tumor necrosis factor family that weakly induces apoptosis." J Biol Chem. Dec. 19, 1997;272(51):32401–10.

Jakubowski et al. "Dual role for TWEAK in angiogenic regulation." J Cell Sci. Jan. 15, 2002;115(Pt 2):267–74.

Nagata (1997) "Apoptosis by Death Factor" Cell 88:355–365.

Pepper MS et al. "Biphasic effect of transforming growth factor–beta 1 on in vitro angiogenesis." Exp Cell Res. Feb. 1993;204(2):356–63.

Wiley et al. (1995) "Identification and Characterization of a New Member of the TNF Family that induces Apoptosis" Immunity 3:673–682.

Ward et al., "Blocking of adhesion molecules in vivo as anti–inflammatory therapy", Ther. Immunol., vol. 1(3), pp. 165–171 (1994).

Ngo et al., "Computational Complexity, Protein Structure Prediction, and the Levinthal Paradox", The Protein Folding Problem, Chapter 14, pp. 435–508 (1994).

Dallman, "Cytokines and transplantation: Th1/Th2 regulation of the immune response to solid organ transplants in the adult", Current Opinion in Immunology, vol. 7, pp. 632–638 (1995).

Krenger and Farrara, "Graft–versus–Host Disease and the Th1/Th2 Paradigm", Immunol. Res., vol. 15, pp. 50–73 (1996).

Abbas AK et al. (eds), Chapter Fifteen, "Immunity to Microbes", *Cellular and Molecular Immunology*, Philadelphia: WB Saunders Co. pp. 302–314 (1991).

Abbas AK et al. (eds), Chapter One, "General Properties of Immune Responses", Introduction to Immunology, *Cellular and Molecular Immunology*, Philadelphia: WB Saunders Co. pp. 4–12 (1991).

Toogood et al., "The Immune Response Following Small Bowel Transplantation", Transplantation, vol. 62(6), pp. 851–855 (1996).

De Wit et al., "Preferential Activation of Th2 Cells in Chronic Graft–versus–Host Reaction", The Journal of Immunology, Col. 150(2), pp. 361–366 (1993).

Williamson et al., "IL–12 Is a Central Mediator of Acute Graft–Versus–Host Disease in Mice", J. Immunol., pp. 689–699 (1996).

Chaplin and Fu, "Cytokine regulation of secondary lymphoid organ development", Current Opinion in Immunology, vol. 10, pp. 288–297 (1998).

Grewal and Flavell, "The CD40 Ligand", Immunol. Res., vol. 16, pp. 59–70 (1997).

Mackay and Browning, "Turning off follicular dendritic cells", Nature, vol. 395, pp. 26–27 (1998).

Flynn et al., "CD4 T Cell Cytokine Differentiation: The B Cell Activation Molecule, OX40 Ligand, Instructs CD4 T Cells to Express Interleukin 4 and Upregulates Expression of the Chemokine Receptor Blr–1", J. Exp. Med., vol. 188, pp. 297–304 (1998).

Lynch et al., "Tweak Induces Proliferation in Endothelial Cells and Substitutes For EGF and Hydrocortisone in Culture", Interferon Cytokine Res., vol. 18, A–46 (1998).

Marsters et al., "Identification of a ligand for the death–domain–containing receptor Apo3", Current Biology, vol. 8, pp. 525–528 (1998).

Ashkenazi and Dixit, "Death Receptors: Signaling and Modulation", Science, vol. 281, pp. 1305–1308 (1998).

Lenschow et al., "Differential Effects of Anti–B7–1 and Anti–B7–2 Monoclonal Antibody Treatment on the Development of Diabetes in the Nonobese Diabetic Mouse", J. Exp. Med., vol. 181, pp. 1145–1155 (1995).

Durie et al., "Antibody to the Ligand of CD40, gp39, Blocks the Occurrence of the Acute and Chronic Forms of Graft–vs–Host Disease", J. Clin. Invest., vol. 94, pp. 1333–1338 (1994).

Grewal and Flavell, "The Role of CD40 Ligand in Costimulation and T–Cell Activation", Immunol. Rev., vol. 153, pp. 85–106 (1996).

Mohan et al., "Interaction Between CD40 and Its Ligand gp39 in the Development of Murine Lupus Nephritis[1]", J. Immunol., vol. 154, pp. 1470–1480 (1995).

Kalled et al., "Anti–CD40 Ligand Antibody Treatment of $SNF_1$ Mice with Established Nephritis: Preservation of Kidney Function", J. Immunol., vol. 160, pp. 2158–2165 (1998).

Bach–Elias et al., "Presence of autoantibodies against small nuclear ribonucleoprotein epitopes in Chagas' patients' sera", Parasitol. Res., vol. 84, pp. 196–799 (1998).

Tibbetts et al., "Cardiac Antigen–Specific Autoantibody Production is Associated with Cardiomyopathy in *Typansoma* cruzi–Infected Mice[1]", J. Immunol., vol. 152, pp. 1493–1499 (1994).

Kirk et al., "CTLA4–Ig and anti–CD40 ligand prevent renal allograft rejection in primates", Proc. Natl. Acad. Sci. USA, vol. 94, pp. 8789–8794 (1997).

Kaplan et al., "Th2 Lymphocytes Kill Antigen Presenting Macrophages Through a TWEAK Dependant Pathway", J. of Investigate Medicine, vol. 46:287A (1998).

Meighan–Mantha et al., "The Mitogen–inducible Fn14 Gene Encodes a Type I Transmembrane Protein that Modulates Fibroblast Adhesion and Migration" J. Biol. Chem., 274: 33166–33176 (Nov. 1999).

Cassiano et al., "Molecular Cloning of a Novel Receptor for TWEAK", Scand. J. Immunol. 51 (Supp. 1) 1–111.

Browning et al., "Characterization of Surface Lymphotoxin Forms" J. Immunol, 154:33–46 (1995).

* cited by examiner

Fig. 1 Effect of Tweak on endothelial cells proliferation. HUVEC were cultured for 3-4 days in basal media supplemented with Tweak in the presence or absence of bFGF and pulsed with $^3$H-Thy for the last 18 hours. Anti-Tweak mAb (10ug/ml) blocks Tweak (100ng/ml) enhancing effect on bFGF (1/500 dilution)

Fig. 2 *Effect of TWEAK on cell death*

Fig.3 Effect of Tweak on endothelial cells migration.

FIGURE 4

METHOD FOR PROMOTING NEOVASCULARIZATION

CROSS-REFERENCE TO RELATED APPLICATIONS

This application is a national stage application (35 U.S.C. § 371) of International application number PCT/US01/14545, filed May 7, 2001, which claims benefit of United States provisional application No. 60/202,738, filed May 8, 2000, the disclosures of which are incorporated by reference herein in their entirety.

FIELD OF INVENTION

The present invention relates to a method for enhancing angiogenic activity to promote neovascularization.

BACKGROUND OF THE INVENTION

Growth of microvasculature, or angiogenesis, involves endothelial cell (EC) proliferation, migration, differentiation, and structural organization into new vessels.

Angiogenic regulators induce changes in endothelial cells (EC) at a variety of levels, including their proliferative, migratory, secretory, and adhesive properties, and may do so through their action on ECs or other cell types (Kumar et al, 1998, Int. J. Oncology 12:749–757; Bussolino et al., 1997, Trends in Biochem, 22:251–256). Several TNF family ligands previously have been implicated in the process of angiogenesis, namely TNFα, FasL and TWEAK.

SUMMARY OF THE INVENTION

TWEAK, a novel member of the TNF ligand family, may promote angiogenesis based on its ability to induce IL-8 production by several epithelial tumor cell lines, proliferation in various human EC and aortic smooth muscle cells under reduced growth factor conditions, and stimulation of an angiogenic response when implanted in rat corneas. Herein, we further characterize the angiogenic potential of TWEAK, demonstrating that TWEAK synergizes with Fibroblast Growth Factor (FGF) to induce proliferation and migration of EC's. While TWEAK weakly promotes EC survival, the synergistic effect of TWEAK and FGF on EC proliferation appears to be due to potentiation of cell division rather than decreased cell death. TWEAK also did not detectably alter the expression of receptors for FGF or VEGF, or expression of the integrins $\alpha_1$, $\alpha_5$, $\alpha_v$, $\beta_1$, or $\beta_3$. The ability of TWEAK to induce ECs to form capillaries in the absence of other cell types was demonstrated in a 3D fibrin gel matrix where, strikingly, TWEAK induced the morphogenesis of lumens in invading, bFGF-dependent EC cords. Our findings further distinguish TWEAK from other TNF family ligands, demonstrating its ability to promote angiogenesis at multiple discrete stages.

One aspect of the present invention is a method for enhancing endothelial cell proliferation in an in vitro culture comprising adding to said culture, a formulation consisting essentially of a synergistically effective amount of a TWEAK agonist and an angiogenic factor.

A second aspect of the present invention is a method for enhancing angiogenic activity in a mammal to promote neovascularization comprising the step of administering to said mammal a formulation comprising a synergistically effective amount of a TWEAK agonist and an angiogenic factor sufficient to promote neovascularization. A preferred embodiment is the use of bFGF.

DETAILED DESCRIPTION

As used herein the terms, "angiogenesis," "revascularization," "increased collateral circulation," and "regeneration of blood vessels" are considered as synonymous.

"Angiogenesis" is defined as any alteration of an existing vascular bed or the formation of new vasculature which benefits tissue perfusion. This includes the formation of new vessels by sprouting of endothelial cells from existing blood vessels or the remodeling of existing vessels to alter size, maturity, direction or flow properties to improve blood perfusion of tissues.

A therapeutic is said to have "therapeutic efficacy" in modulating angiogenesis and an amount of the therapeutic is said to be a "angiogenic modulatory amount", if administration of that amount of the therapeutic is sufficient to cause a significant modulation (i.e., increase or decrease) in angiogenic activity when administered to a subject (e.g., an animal model or human patient) needing modulation of angiogenesis.

The term angiogenic factor refers to factors which promote the angiogenic process, including but not limited to the following phases of the process, ie. the degradation of the extracellular matrix, cell proliferation, cell migration and structural organization (Kumar et al, 1998, Int. J. Oncology 12:749–757; Bussolino et al., 1997, Trends in Biochem, 22:251–256). Angiogenic factors include but are not limited to fibroblast growth factor (bFGF), acidic FGF (aFGF), FGF-5, vascular endothelial growth factor isoforms (VEGF), angiopoietin-1 (Ang-1) and angiopoietin-2 (Ang-2), Platelet-derived endothelial cell growth factor (PD-ECGF), hepatocyte growth factor (HGF), interleukin-8 (IL-8), granulocyte-colony stimulating factor (G-CSF), placental growth factor, proliferin, B61, soluble vascular cell adhesion molecular-1, soluble E-selection, 12-hydrozyeicosatetraenoic acid, Tat protein of HIV-1, angiogenin, TNFα, FasL, Transforming growth factor-β.

As used herein, the ability of TWEAK to act synergistically with another angiogenic factor means that the combination of TWEAK and the angiogenic factor induce a response that is greater than the sum of the responses to either agent alone, as measured in one or more in vitro assays which measure stages of the angiogenic process. These include but are not limited to endothelial cell survival, proliferation, migration, or capillary tube formation, as described herein.

The term "pharmaceutically acceptable" when referring to a natural or synthetic substance means that the substance has an acceptable toxic effect in view of its much greater beneficial effect, while the related the term, "physiologically acceptable," means the substance has relatively low toxicity.

As used herein, the term "antibody homolog" includes intact antibodies consisting of immunoglobulin light and heavy chains linked via disulfide bonds. The term "antibody homolog" is also intended to encompass a TWEAK therapeutic comprising one or more polypeptides selected from immunoglobulin light chains, immunoglobulin heavy chains and antigen-binding fragments thereof which are capable of binding to one or more antigens (i.e., TWEAK or patched).

The component polypeptides of an antibody homolog composed of more than one polypeptide may optionally be disulfide-bound or otherwise covalently crosslinked. Accordingly, therefore, "antibody homologs" include intact immunoglobulins of types IgA, IgG, IgE, IgD, IgM (as well as subtypes thereof), wherein the light chains of the immunoglobulin may be of types kappa or lambda or portions of intact antibodies that retain antigen-binding specificity, for example, Fab fragments, Fab' fragments, F(ab')2 fragments, F(v) fragments, heavy chain monomers or dimers, light chain monomers or dimers, dimers consisting of one heavy and one light chain, and the like.

As used herein, a "humanized antibody homolog" is an antibody homolog, produced by recombinant DNA technology, in which some or all of the amino acids of a human immunoglobulin light or heavy chain that are not required for antigen binding have been substituted for the corresponding amino acids from a nonhuman mammalian immunoglobulin light or heavy chain. A "human antibody homolog" is an antibody homolog in which all the amino acids of an immunoglobulin light or heavy chain (regardless of whether or not they are required for antigen binding) are derived from a human source.

An "amino acid" is a monomeric unit of a peptide, polypeptide, or protein. There are twenty amino acids found in naturally occurring peptides, polypeptides and proteins, all of which are L-isomers. The term also includes analogs of the amino acids and D-isomers of the protein amino acids and their analogs.

The term "bioavailability" refers to the ability of a compound to be absorbed by the body after administration. For instance, a first compound has greater bioavailability than a second compound if, when both are administered in equal amounts, the first compound is absorbed into the blood to a greater extent than the second compound.

An "expression vector" is a polynucleotide, such as a DNA plasmid or phage (among other common examples) which allows expression of at least one gene when the expression vector is introduced into a host cell. The vector may, or may not, be able to replicate in a cell.

The phrase "extracellular signaling protein" means any protein that is either secreted from a cell, or is associated with the cell membrane, and upon binding to the receptor for that protein on a target cell, triggers a response in the target cell.

A "functional equivalent" of an amino acid residue is (i) an amino acid having similar reactive properties as the amino acid residue that was replaced by the functional equivalent; (ii) an amino acid of a ligand of a polypeptide of the invention, the amino acid having similar properties as the amino acid residue that was replaced by the functional equivalent; (iii) a non-amino acid molecule having similar properties as the amino acid residue that was replaced by the functional equivalent.

"Heterologous promoter"- as used herein is a promoter which is not naturally associated with a gene or a purified nucleic acid.

"Homology" and "identity" each refer to sequence similarity between two polypeptide sequences, and both 'homology and 'identity' are used interchangeably in this disclosure. Homology can be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology between sequences is a function of the number of matching or homologous positions shared by the sequences. An "unrelated" or "non-homologous" sequence shares less than 40 percent identity, though preferably less than 25 percent identity, with a sequence of the present invention.

For instance, if 6 of 10 of the positions in two sequences are matched or are homologous, then the two sequences are 60% homologous. By way of example, the DNA sequences CTGACT and CAGGTT share 50% homology (3 of the 6 total positions are matched). Generally, a comparison is made when two sequences are aligned to give maximum homology. Such alignment can be provided using, for instance, the method of Needleman et al., *J. Mol Biol.* 48:443–453 (1970), implemented conveniently by computer programs described in more detail below. Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354–352, Nat. Biomed. Res. Foundation, Washington, D.C. (1978).

"Percent homology/identity" of two amino acids sequences or two nucleic acid sequences is determined using the alignment algorithm of Karlin and Altschul (Proc. Nat. Acad. Sci., USA 87: 2264 (1990) as modified in Karlin and Altschul (Proc. Nat. Acad. Sci., USA 90: 5873 (1993). Such an algorithm is incorporated into the NBLAST or XBLAST programs of Altschul et al., J. Mol. Biol. 215: 403 (1990). BLAST searches are performed with the NBLAST program, score=100, wordlength=12, to obtain nucoetide sequences homologous to a nucleic acid of the invention. BLAST protein searches are performed with the XBLAST program, score=50, wordlength=3, to obtain amino acid sequences homologous to a reference polypeptide. To obtain gapped alignments for comparisons, gapped BLAST is used as described in Altschul et al., Nucleic Acids Res., 25: 3389 (1997). When using BLAST and Gapped BLAST, the default parameters of the respective programs (XBLAST and NBLAST) are used. See http://www/ncbi.nlm.nih.gov The term "hydrophobic" refers to the tendency of chemical moieties with nonpolar atoms to interact with each other rather than water or other polar atoms. Materials that are "hydrophobic" are, for the most part, insoluble in water. Natural products with hydrophobic properties include lipids, fatty acids, phospholipids, sphingolipids, acylglycerols, waxes, sterols, steroids, terpenes, prostaglandins, thromboxanes, leukotrienes, isoprenoids, retenoids, biotin, and hydrophobic amino acids such as tryptophan, phenylalanine, isoleucine, leucine, valine, methionine, alanine, proline, and tyrosine. A chemical moiety is also hydrophobic or has hydrophobic properties if its physical properties are determined by the presence of nonpolar atoms.

The phrase "internal amino acid" means any amino acid in a peptide sequence that is neither the N-terminal amino acid nor the C-terminal amino acid.

"Isolated" (used interchangeably with "substantially pure") when applied to nucleic acid i.e., polynucleotide sequences that encode polypeptides, means an RNA or DNA polynucleotide, portion of genomic polynucleotide, cDNA or synthetic polynucleotide which, by virtue of its origin or manipulation: (i) is not associated with all of a polynucleotide with which it is associated in nature (e.g., is present in a host cell as an expression vector, or a portion thereof); or (ii) is linked to a nucleic acid or other chemical moiety other than that to which it is linked in nature; or (iii) does not occur in nature. By "isolated" it is further meant a polynucleotide sequence that is: (i) amplified in vitro by, for example, polymerase chain reaction (PCR); (ii) synthesized chemically; (iii) produced recombinantly by cloning; or (iv) purified, as by cleavage and gel separation.

"Isolated" (used interchangeably with "substantially pure") when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature, for example, a protein that is chemically manipulated by appending, or adding at least one hydrophobic moiety to the protein so that the protein is in a form not found in nature. By "isolated" it is further meant a protein that is: (i) synthesized chemically; or (ii) expressed in a host cell and purified away from associated and contaminating proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

A "protein" is any polymer consisting essentially of any of the 20 amino acids. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

The terms "peptide(s)", "protein(s)" and "polypeptide(s)" are used interchangeably herein. The terms "polynucleotide sequence" and "nucleotide sequence" are also used interchangeably herein.

"Recombinant," as used herein, means that a protein is derived from recombinant, mammalian expression systems.

Thus, "substantially pure nucleic acid" is a nucleic acid which is not immediately contiguous with one or both of the coding sequences with which it is normally contiguous in the naturally occurring genome of the organism from which the nucleic acid is derived. Substantially pure DNA also includes a recombinant DNA which is part of a hybrid gene encoding additional TWEAK sequences.

The amounts of a TWEAK agonist and angiogenic factor required to be effective in enhancing angiogenic activity for promoting neovascularization will, of course, vary with the individual being treated and is ultimately at the discretion of the physician. The factors to be considered include the condition of the patient being treated, the efficacy of the particular TWEAK agonist being used, the nature of the formulation, and the patient's body weight. While it possible to administer and a TWEAK agonist simultaneously, it is also contemplated that angiogenic factor can be given as a bolus before starting the infusion of the TWEAK agonist. It is also contemplated that angiogenic factor can be administered after the infusion of the TWEAK agonist.

TWEAK agonists include those taught in WO98/05783, WO98/35061 and WO99/19490. Such TWEAK agonists include soluble recombinant TWEAK protein.

"Standard hybridization conditions" refer to salt and temperature conditions substantially equivalent to 0.5×SSC to about 5×SSC and 65° C. for both hybridization and wash. The term "standard hybridization conditions" as used herein is therefore an operational definition and encompasses a range of hybridization conditions. Nevertheless, for the purposes of this present disclosure "high stringency" conditions include hybridizing with plaque screen-buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulfate, and 100 µg/ml denatured, sonicated salmon sperm DNA at 65° C. for 12–20 hours, and washing with 75 mM NaCl/7.5 mM sodium citrate (0.5×SSC)/1% SDS at 65° C. "Low stringency" conditions include hybridizing with plaque screen buffer, 10% dextran sulfate and 110 µg/ml denatured, sonicated salmon sperm DNA at 55° C. for 12–20 hours, and washing with 300 mM NaCl/30 mM sodium citrate (2.0× SSC)/1% SDS at 55° C. See also Current Protocols in Molecular Biology, John Wiley & Sons, Inc. New York, Sections 6.3.1–6.3.6, (1989).

A "therapeutic composition" as used herein is defined as comprising the therapeutics of the invention and other biologically compatible ingredients. The therapeutic composition may contain excipients such as water, minerals and carriers such as protein.

"Wild type" means the naturally-occurring polynucleotide sequence of an exon of a protein, or a portion thereof, or protein sequence, or portion thereof, respectively, as it normally exists in vivo.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. Unless stipulated otherwise, all references cited in the Detailed Description are incorporated herein by reference.

A. Production of Fragments and Analogs

Fragments of an isolated protein (e.g., fragments of TWEAK) can also be produced efficiently by recombinant methods, by proteolytic digestion, or by chemical synthesis using methods known to those of skill in the art. In recombinant methods, internal or terminal fragments of a polypeptide can be generated by removing one or more nucleotides from one end (for a terminal fragment) or both ends (for an internal fragment) of a DNA sequence which encodes for the isolated TWEAK polypeptide. Expression of the mutagenized DNA produces polypeptide fragments. Digestion with "end nibbling" endonucleases can also generate DNAs which encode an array of fragments. DNAs which encode fragments of a protein can also be generated by random shearing, restriction digestion, or a combination or both. Protein fragments can be generated directly from intact proteins. Peptides can be cleaved specifically by proteolytic enzymes, including, but not limited to plasmin, thrombin, trypsin, chymotrypsin, or pepsin. Each of these enzymes is specific for the type of peptide bond it attacks. Trypsin catalyzes the hydrolysis of peptide bonds in which the carbonyl group is from a basic amino acid, usually arginine or lysine. Pepsin and chymotrypsin catalyse the hydrolysis of peptide bonds from aromatic amino acids, such as tryptophan, tyrosine, and phenylalanine. Alternative sets of cleaved protein fragments are generated by preventing cleavage at a site which is suceptible to a proteolytic enzyme. For instance, reaction of the ε-amino acid group of lysine with ethyltrifluorothioacetate in mildly basic solution yields blocked amino acid residues whose adjacent peptide bond is no longer susceptible to hydrolysis by trypsin. Proteins can be modified to create peptide linkages that are susceptible to proteolytic enzymes. For instance, alkylation of cysteine residues with β-haloethylamines yields peptide linkages that are hydrolyzed by trypsin (Lindley, (1956) Nature 178, 647). In addition, chemical reagents that cleave peptide chains at specific residues can be used. For example, cyanogen bromide cleaves peptides at methionine residues (Gross and Witkip, (1961) J. Am. Chem. Soc. 83, 1510). Thus, by treating proteins with various combinations of modifiers, proteolytic enzymes and/or chemical reagents, the proteins may be divided into fragments of a desired length with no overlap of the fragments, or divided into overlapping fragments of a desired length.

Fragments can also be synthesized chemically using techniques known in the art such as the Merrifield solid phase F moc or t-Boc chemistry. Merrifield, Recent Progress in Hormone Research 23: 451 (1967).

B. Production of Altered DNA and Peptide Sequences: Random Methods

Amino acid sequence variants of a protein can be prepared by random mutagenesis of DNA which encodes the protein or a particular portion thereof. Useful methods include PCR mutagenesis and saturation mutagenesis. A library of random amino acid sequence variants can also be generated by the synthesis of a set of degenerate oligonucleotide sequences. Methods of generating amino acid sequence variants of a given protein using altered DNA and peptides are well-known in the art. The following examples of such methods are not intended to limit the scope of the present invention, but merely serve to illustrate representative techniques. Persons having ordinary skill in the art will recognize that other methods are also useful in this regard.

PCR Mutagenesis: See, for example Leung et al., (1989) Technique 1, 11–15.

Saturation Mutagenesis: One method is described generally in Mayers et al., (1989) Science 229, 242.

Degenerate Oligonucleotide Mutagenesis: See for example Harang, S. A., (1983) Tetrahedron 39, 3; Itakura et al., (1984) Ann. Rev. Biochem. 53, 323 and Itakura et al., Recombinant DNA, Proc. 3rd Cleveland Symposium on Macromolecules, pp. 273–289 (A. G. Walton, ed.), Elsevier, Amsterdam, 1981.

C. Production of Altered DNA and Peptide Sequences: Directed Methods

Non-random, or directed, mutagenesis provides specific sequences or mutations in specific portions of a polynucleotide sequence that encodes an isolated polypeptide, to provide variants which include deletions, insertions, or substitutions of residues of the known amino acid sequence of the isolated polypeptide. The mutation sites may be modified individually or in series, for instance by: (1) substituting first with conserved amino acids and then with more radical choices depending on the results achieved; (2) deleting the target residue; or (3) inserting residues of the same or a different class adjacent to the located site, or combinations of options 1–3.

Clearly, such site-directed methods are one way in which an N-terminal cysteine (or a functional equivalent) can be introduced into a given polypeptide sequence to provide the attachment site for a hydrophobic moiety.

Alanine scanning Mutagenesis: See Cunningham and Wells, (1989) Science 244, 1081–1085).

Oligonucleotide-Mediated Mutagenesis: See, for example, Adelman et al., (1983) DNA 2, 183.

Cassette Mutagenesis: See Wells et al., (1985) Gene 34, 315.

Combinatorial Mutagenesis: See, for example, Ladner et al., WO 88/06630

Methods of Treatment

The method of the present invention are useful as a treatment in diseases where enhanced angiogenic activity is desirable to promote neovascularization. Such diseases and conditions include: myocardial ischemic conditions (e.g., myocardial infarction, improve blood flow in patients with coronary artery disease suffering from myocardial ischemia or inadequate blood flow to areas other than the heart such as in peripheral vascular disease, where decreased blood flow is a problem, revascularization of necrotic tissue, for example of the myocardium after an infarction or an angioplasty, angina, heart transplants, vascular grafts, and reopening vessels to improve vascularization, perfusion, collagenization and organization of said lesions), wound healing, and tissue and organ transplantations (e.g., enhancement of autologous or heterologous microvascular transplantation). Promotion of wound healing includes healing of incisions, bone repair, bum healing, post-infarction repair in myocardial injury, healing of gastric ulcers and other ulcers of the gastrointestinal tract and generally in promoting the formation, maintenance and repair of tissue. Neovascularization of grafted or transplanted tissue is also contemplated, especially in subjects suffering from vascular insufficiency, such as diabetic patients.

As a general matter, the methods of the present invention may be utilized for any mammalian subject needing modulation of angiogenesis. Mammalian subjects which may be treated according to the methods of the invention include, but are not limited to, human subjects or patients. In addition, however, the invention may be employed in the treatment of domesticated mammals which are maintained as human companions (e.g., dogs, cats, horses), which have significant commercial value (e.g., dairy cows, beef cattle, sporting animals), which have significant scientific value (e.g., captive or free specimens of endangered species), or which otherwise have value. In addition, as a general matter, the subjects for treatment with the methods of the present invention need not present indications for treatment with the agents of the invention other than those indications associated with need for modulation of angiogenesis. That is, the subjects for treatment are expected to be otherwise free of indications for treatment with the TWEAK therapeutic agents of the invention.

One of ordinary skill in the medical or veterinary arts is trained to recognize subjects which may need modulation of angiogenesis. In particular, clinical and non-clinical trials, as well as accumulated experience, relating to the presently disclosed and other methods of treatment, are expected to inform the skilled practitioner in deciding whether a given subject is in need of modulation and whether any particular treatment is best suited to the subject's needs, including treatment according to the present invention.

Accordingly, the methods of this invention may employ TWEAK agonists or biologically active portions thereof, and angiogenic factors, to promote angiogenesis, such as, to repair damage of myocardial tissue as a result of myocardial infarction. Such methods may also include the repair of the cardiac vascular system after ischemia including the growth of collateral vasculature. Methods utilizing TWEAK agonists and angiogenic factors may be employed to stimulate the growth of transplanted tissue and collateral vasculature where coronary bypass surgery is performed. Methods may also treat damaged vascular tissue as a result of coronary artery disease and peripheral or central nervous system vascular disease or ischemia Methods of the invention may also promote wound healing, particularly to re-vascularize damaged tissues or stimulate collateral blood flow during ischemia and where new capillary angiogenesis is desired. Other methods of the invention may be employed to treat full-thickness wounds such as dermal ulcers, including pressure sores, venous ulcers, and diabetic ulcers. In addition, methods employing TWEAK therapeutics may be employed to treat full-thickness burns and injuries where a skin graft or flap is used to repair such burns and injuries. Such TWEAK agonists and angiogenic factors may also be employed for use in plastic surgery, for example, for the repair of lacerations, burns, or other trauma. In urology, methods of the invention may assist in recovery of erectile function.

Since angiogenesis is important in keeping wounds clean and non-infected, methods may be employed in association with surgery and following the repair of cuts. They may also be employed for the treatment of abdominal wounds where there is a high risk of infection. Methods using TWEAK therapeutics described herein may be employed for the promotion of endothelialization in vascular graft surgery. In the case of vascular grafts using either transplanted or synthetic material, TWEAK agonists and angiogenic factors can be applied to the surface of the graft or at the junction to promote the growth of vascular smooth muscle and adventitial cells in conjunction with endothelial cells.

Methods of the invention may also be employed to coat artificial prostheses or natural organs which are to be transplanted in the body to minimize rejection of the transplanted material and to stimulate vascularization of the transplanted materials and may also be employed for vascular tissue repair, for example, that occurring during arteriosclerosis and required following balloon angioplasty where vascular tissues are damaged. Specifically, methods of the invention may be employed to promote recovery from arterial wall injury and thereby inhibit restenosis.

Nucleic acid sequences encoding TWEAK agonists may also be employed for in vitro purposes related to scientific research, synthesis of DNA and manufacture of DNA vectors, and for the production of diagnostics and therapeutics to treat human disease. For example, methods of the invention may involve in vitro culturing of vascular smooth muscle cells, fibroblasts, hematopoietic cells, muscle, myotendonous junction, bone or cartilage- derived cells and other mesenchymal cells, where a TWEAK therapeutic is added to the conditional medium in a concentration from 10 ng/ml to 20 ug/ml.

These therapeutic agents may be administered by any route which is compatible with the particular agent employed. The therapeutic agents of the invention may be provided to an individual by any suitable means, preferably directly (e.g., locally, as by injection or topical administration to a tissue locus) or systemically (e.g., parenterally or orally). Where the agent is to be provided parenterally, such as by intravenous, intraarterial, subcutaneous, or intramuscular, administration, the agent preferably comprises part of an aqueous solution. The solution is physiologically acceptable so that in addition to delivery of the desired agent to the subject, the solution does not otherwise adversely affect the subject's electrolyte and/or volume balance. The aqueous medium for the therapeutic may comprise normal physiologic saline (e.g., 9.85% NaCl, 0.15M, pH 7–7.4).

The therapeutics are preferably administered as a sterile pharmaceutical composition containing a pharmaceutically acceptable carrier, which may be any of the numerous well known carriers, such as water, saline, phosphate buffered saline, dextrose, glycerol, ethanol, and the like, or combinations thereof. The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, tris(hydroxymethyl) methylamine and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

Pharmaceutical compositions of TWEAK agonists and angiogenic factors comprise any of the compounds of the present invention, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Injection Delivery

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant.

Controlled release administration of a particular therapeutic may be useful. For example, the therapeutic may be administered using intravenous infusion, an implantable osmotic pump, a transdermal patch, liposomes, or other modes of administration. In one embodiment, a pump may be used [Langer et al., eds., Medical Applications of Controlled Release, CRC Pres., Boca Raton, Fla. (1974); Sefton, CRC Crit. Ref. Biomed. Eng., 14:201 (1987); Buchwald et al., Surgery, 88:507 (1980); Saudek et al., N. Engl. J. Med., 321:574 (1989)]. In another embodiment, polymeric materials can be used [see, Langer, 1974, supra; Sefton, 1987, supra; Smolen et al., eds., Controlled Drug Bioavailability, Drug Product Design and Performance, Wiley, N.Y. (1984); Ranger et al., J. Macromol. Sci. Rev. Macromol. Chem., 23:61 (1983); see also Levy et al., Science, 228:190 (1985); During et al., Ann. Neurol., 25:351 (1989); Howard et al., J. Neurosurg., 71:105 (1989)]. In yet another embodiment, a controlled release system can be placed in proximity of the therapeutic target, e.g., a tumor, thus requiring only a fraction of the systemic dose [see. e.g., Goodson, in Medical Applications of Controlled Release, vol. 2, pp. 115–138 (1984)]. Other controlled release systems are discussed in the review by Langer, Science, 249:1527–1533 (1990). In another embodiment, the therapeutic compound can be delivered in a vesicle, in particular a liposome (see Langer, 1990, supra); Treat et al., in Liposomes in the Therapy of Infectious Disease and Cancer, Lopez-Berestein and Fidler (eds.), Liss, New York, pp. 353–365 (1989); Lopez-Berestein, pp. 317–327; see generally id.).

Oral Delivery

Contemplated for use herein are oral solid dosage forms, which are described generally in Martin, Chapter 89, 1990, supra, which is herein incorporated by reference. Solid dosage forms include-tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, in Modem Pharmaceutics, Chapter 10, Banker and Rhodes ed., (1979), herein incorporated by reference. In general, the formulation will include the therapeutic (or chemically modified form), and inert ingredients which allow for protection against the stomach environment, and release of the biologically active material in the intestine.

For the protein (or derivative) the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine. To ensure full gastric resistance, a coating impermeable to at least pH 5.0 is essential. Examples of the more common inert ingredients that are used as enteric coaungs are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films. A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression. Colorants and flavoring agents may all be included. For example, the protein (or derivative) may be formulated (such as by liposorne or microsphere encapsulation) and then further contained within an edible product, such as a refrigerated beverage containing colorants and flavoring agents. One may dilute or increase the volume of the therapeutic with an inert material. These diluents could include carbohydrates, especially mannitol, alpha-lactose, anyhydrous lactose, cellulose, sucrose, modified dextrans and starch. Certain inorganic salts may be also be used as fillers including calcium triphosphate, magnesium carbonate and sodium chloride. Some commercially available diluents are FAST-FLO™, EMDEX™, STA-RX 1500™, EMCOMPRESS™ and AVICELL™. Disintegrants may be included in the formulation of the therapeutic into a solid dosage form. Materials used as disintegrants include but are not limited to starch including the commercial disintegrant based on starch, EXPLOTAB™, Sodium starch glycolate, AMBERLITE™, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutics. An antifrictional agent may be included in the formulation of the therapeutic to prevent sticking during the formulation process. Lubricants may be used as a layer between the therapeutic and the die wall, and these can include but are not limited to: stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, and CARBOWAX 4000™ and 6000™. Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent.

Surfactants may include anionic detergents such as sodium lauryl sulfate, dioctyl sodium-sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios. Additives which potentially enhance uptake of the protein (or derivative) are for instance the fatty acids oleic acid, linoleic acid and linolenic acid.

Pulmonary Delivery

Also contemplated herein is pulmonary delivery of the present proteins (or derivatives thereof). The protein (or derivative) is delivered to the lungs of a mammal while inhaling and traverses across the lung epithelial lining to the blood-stream. Other reports of this include Adjei et al., Pharmaceutical Research, 7(6):565–569 (1990); Adjei et al., International Journal of Pharmaceutics, 63:135–144 (1990) (leuprolide acetate); Braquet et al., Journal of Cardiovascular Pharmacology, 13(suppl. 5): 143–146 (1989) (endothelin-1); Hubbard et al., Annals of Internal Medicine, 3(3):206–212 (1989) (alpha 1-antitrypsin); Smith et al., J. Clin. Invest., 84:1145–1146 (1989) (alpha 1-proteinase); Oswein et al., "Aerosolization of Proteins", Proceedings of Symposium on Respiratory Drug Delivery II, Keystone, Colo., (March 1990) (recombinant human growth hormone); Debs et al., J. Immunol., 140:3482–3488 (1988) (interferon-gamma and tumor necrosis factor alpha) and Platz et al., U.S. Pat. No. 5,284,656 (granulocyte colony stimulating factor). Contemplated for use in the practice of this invention are a wide range of mechanical devices designed for pulmonary delivery of therapeutic products, including but not limited to nebulizers, metered-dose inhalers, and powder inhalers, all of which are familiar to those skilled in the art.

Some specific examples of commercially available devices suitable for the practice of this invention are the ULTRAVENT™ nebulizer, manufactured by Mallinckrodt, Inc., St. Louis, Mo.; the ACORN II™ nebulizer, manufactured by Marquest Medical Products, Englewood, Colo.; the VENTOLIN METERED-DOSE™ inhaler, manufactured by Glaxo Inc., Research Triangle Park, N.C.; and the SPIN-HALER POWDER™ inhaler, manufactured by Fisons Corp., Bedford, Mass. All such devices require the use of formulations suitable for the dispensing of protein (or derivative) . Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified protein may also be prepared in different formulations depending on the type of chemical modifications or the type of device employed.

Formulations suitable for use with a nebulizer, either jet or ultrasonic, will typically comprise protein (or derivative) dissolved in water at a concentration of about 0.1 to 25 mg of biologically active protein per ml of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the protein (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing protein (or derivative) and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 mu m (or microns), most preferably 0.5 to 5 mu m, for most effective delivery to the distal lung.

Dosages

For all of the above molecules, as further studies are conducted, information will emerge regarding appropriate dosage levels for treatment of various conditions in various patients, and the ordinary skilled worker, considering the therapeutic context, age and general health of the recipient, will be able to ascertain the proper dosage. Generally, for injection or infusion, dosage will be between 0.01 mu g of biologically active protein/kg body weight, (calculating the mass of the protein alone, without chemical modification), and 10 mg/kg (based on the same). The dosing schedule may vary, depending on the circulation half-life of the protein or derivative used, whether the polypeptide is delivered by bolus dose or continuous infusion, and the formulation used.

Administration with Other Compounds

For therapy associated with modulating angiogenesis, one may administer the present TWEAK agonists (or derivatives) and angiogenic factors in conjunction with one or more pharmaceutical compositions used for treating other clinical complications of the need for angiogenic modulation, such as those used for treatment of cancer (e.g., chemotherapeutics), cachexia, high blood pressure, high cholesterol, and other adverse conditions. Administration may be simultaneous or may be in seriatim.

Nucleic Acid-Based Therapeutic Treatment

Nucleic acid sequences encoding a TWEAK agonist could be introduced into human tumor or blood vessel cells to develop gene therapy.

In one embodiment, a nucleic acid sequence encoding a TWEAK agonist is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, adipose tissue can be specifically targeted. Examples of particular vectors include, but are not limited to, a defective herpes virus 1 (HSV1) vector [Kaplitt et al., Molec. Cell. Neurosci., 2:320–330 (1991)], an attenuated adenovirus vector, such as the vector described by Stratford-Perricaudet et al., J. Clin. Invest., 90:626–630 (1992), and a defective adeno-associated virus vector [Samulski et al., J. Virol., 61:3096–3101 (1987); Samulski et al., J. Virol., 63:3822–3828 (1989)]. In another embodiment, the nucleic acid can be introduced in a retroviral vector, e.g., as described in Anderson et al., U.S. Pat. No. 5,399,346; Mann et al., Cell, 33:153 (1983); Temin et al., U.S. Pat. No. 4,650,764; Temin et al., U.S. Pat. No. 4,980,289; Markowitz et al., J. Virol., 62:1120 (1988); Temin et al., U.S. Pat. No. 5,124,263; International Patent Publication No. WO 95/07358, published Mar. 16, 1995, by Dougherty et al.; and Kuo et al., Blood, 82:845 (1993). Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner et al., Proc. Natl. Acad. Sci. USA, 84:7413–7417 (1987); see Mackey et al., Proc. Natl. Acad. Sci. USA, 85:8027–8031 (1988)]. The use of cationic lipids may promote encapsulation of negatively charged nucleic acids, and also promote fusion with negatively charged cell membranes [Felgner et al., Science, 337:387–388 (1989)]. The use of lipofection to introduce exogenous genes into specific organs in vivo has certain practical advantages. Molecular targeting of liposomes to specific cells represents one area of benefit. It is clear that directing transfection to particular cell types would be particularly advantageous in a tissue with cellular heterogeneity, such as the pancreas, liver, kidney, and brain. Lipids may be chemically coupled to other molecules for the purpose of targeting (see Mackey et al., 1988, supra). Targeted peptides, e.g., hormones or neurotransmitter, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., J. Biol. Chem., 267:963–967 (1992); Wu et al., J. Biol. Chem., 263:14621–14624 (1988); Hartmut et al., Canadian Patent Application No. 2,012,311, filed Mar. 15, 1990).

It is also possible to introduce the vector in vivo in conjunction with a catheter or other device. See Vale et al., 1999; Kornowski et al., 2000.

EXAMPLES

The following examples illustrate aspects of the present invention but should not be construed as limitations. The symbols and convention used in these examples are consistent with those used in contemporary medical and scientific literature Experimental Procedures Cells—Human Umbilical Vein Endothelial Cells (HUVEC) were obtained from Cell System Corporation (CS-C) (Kirkland, Wash.) or Clonetics (San Diego, Calif.) and Human Pulmonary Artery Endothelial Cells (HPAEC), Human Lung Microvascular Endothelial cells (HMVEC-L) and Human Dermal Microvascular Endothelial cells (HMVEC-D) were purchased from Clonetics. HUVEC were routinely passaged in CS-C Medium and used in experiments until passage seven. The other primary cells were routinely passaged in Microvascular Endothelial Cell Growth Medium-2 (EGM2-MV) (Clonetics). EC Basal Medium (EBM) containing 2% fetal bovine serum (FBS), defined as "basal media", and EBM containing 2% FBS and supplier growth supplements, defined as "complete media", were used in proliferation, migration and immunofluorescent staining experiments. EC Basal Medium 2 (EBM-2) and supplier growth supplements were used in the capillary tube formation assay as specified.

Reagents and Antibodies—Recombinant human bFGF was obtained as a growth supplier supplement (Clonetics), bFGF also was purchased from R&D Systems (Minneapolis, Minn.) and Sigma (St.Louis, Mo.). Annexin V-FITC was from Pharmingen (San Diego, Calif.), propidium iodide (PI) from Sigma (St.Louis, Mo.), rabbit anti-human Flk-1 and rabbit anti-Flt-1 antibodies from Research Diagnostics Inc. (Flanders, N.J.), mouse anti-Flg monoclonal antibody (mAb) from Chemicon (Temecula, Calif.), mouse anti-human-$\beta_3$ mouse anti-human-$\beta_1$ (clone LIA ½) and rat anti-human $\alpha_v$ mAbs from Immunotech (Westbrook, Me.), mouse anti-human $\alpha_5$ from Pharmingen (San Diego, Calif.), mouse anti-human $\alpha_1$ (clone AJH10) from Biogen (Gotwals P. J, et al., 1999. Biochem. 38:8280–8288), Phycoerythrin (PE)-conjugated donkey anti-rabbit IgG, goat anti-mouse IgG and donkey anti-rat IgG from Jackson Immunoresearch Labs Inc. (West Groove, Pa.), biotin-conjugated anti-FLAG from Eastman Kodak Company (New Haven, Conn.), and RPE-Streptavidin from Southern Biotechnology Associates, Inc. (Birmingham, Ala.). Soluble CD40L was prepared at Biogen as previously described (Karpusas, M., et al., 1995. Structure 3:1426-xxx).

TWEAK-specific mAbs BE.B3 and AB.D3 were generated in Armenian hamsters by immunizing with soluble human TWEAK protein and standard hybridoma generation procedures. The ability of AB.D3 to bind to human and murine TWEAK and BE.B3 to bind to human TWEAK was demonstrated in an ELISA assay using recombinant soluble TWEAK proteins immobilized on 96 well microtiter plates. The blocking activity of AB.D3 was demonstrated by the ability of this mAb but not BE.B3 to inhibit soluble FLAG-tagged human TWEAK binding to HT29 cells in a FACS analysis. BE.B3 was biotinylated prepared using ImmunoPure Biotinylation kits following the manufacturer's protocol (Pierce, Rockford, Ill.). A hamster control Ig (clone Ha4/8-3.1) was obtained from the American Type Culture Collection and mAb purified from culture supernatant by Protein A Fast Flow column (Pharmacia, Piscataway, N.J.).

Recombinant Soluble Human TWEAK protein—Soluble expression construct for myc-tagged human TWEAK was constructed as previously described (Chicheportiche, Y., et al. 1997. J. Biol. Chem. 272:32401–32410). Flag-tagged and nontagged forms also were made. These soluble forms of TWEAK were expressed in yeast, *Pichia pastoris* strain GS115, using standard conditions.

Proliferation Assays—HVEC were plated in 96-well microtiter plates at subconfluence (4000 cells per well) and cultured overnight in CS-C Medium without addition of supplier growth supplements. Media was replaced with complete Media, or with basal media as defined above. Cells were cultured in basal media with or without TWEAK (100 ng/ml), bFGF using a ⅕₀₀–⅟₁₀₀₀ dilution of bFGF growth supplement (Clonetics) or 1 ng/ml (R&D Systems), VEGF (10 ng/ml) or combinations of these factors. Where indicated, 10 μg/ml anti-TWEAK mAbs AB.D3, BE.B3 or hamster control Ig Ha4/8 also were added. Cells were incubated at 37° C. with 5% $CO_2$ for three days and proliferation was measured by pulsing with $^3$H-Thymidine for the last 10 hours of culture. Cell-bound radioactivity was measured with a Betaplate™ (EG&G Wallac, Gaithersburg, Md.).

Analysis of Apoptosis—HUVEC seeded in 6-well plates at a density of $1.2\times10^5$ cells per well were incubated over night in CS-C Medium without supplier growth supplements. Media was replaced with complete media, or with basal media with or without TWEAK (200 ng/ml), bFGF (1 ng/ml) or combinations of these factors and cells were cultured for 24 hours. Cells were washed with Phosphate buffered saline (PBS) and detached by incubation with dispase (CS-C) for 15 minutes at 37° C. followed by replacement with PBS containing 5 mM EDTA and 0.1% BSA for 15 minutes at 37° C. After an additional wash in PBS, cells were stained with FITC-Annexin-V and $5 \mu g/ml$ Propidium Iodide according to the supplier (Pharmingen). Fluorescence was analyzed within the hour using FACStar-$^{PLUS}$ (Becton Dickinson, San Jose, Calif.).

Endothelial Wound Repair Assay—A standard wound repair assay was employed as previously described (Bussolino F., et al, 1991. J. Clin. Invest. 87:986–991). In brief, a confluent monolayer of HUVEC was grown in CS-C Medium in 35×10 mm cell culture dishes with 2 mm grids (Nalge Nunc International, Naperville, Ill.). The monolayer was wounded by two perpendicular strokes across the diameter of the dish with a 1 mm tip (Morales D. E., et al., 1995. Circulation 91:755–763). Dislodged cells were aspirated and plates were rinsed with PBS. Cells were cultured in complete media, or in fresh basal media with or without TWEAK (200 ng/nl), bFGF ($\frac{1}{1000}$ or 1 ng/ml), VEGF (10 ng/ml) or combinations of these and were incubated for 18 hours at 37° C. with 5% $CO_2$ at which time plates were fixed with 1% paraformaldehyde and stained with Harris Hematoxylin (Sigma, St. Louis, Mo.). Wound repair was quantified by visually counting the number of grids in which the gap was obscured by migrating cells. This number was divided by the total number of grids that aligned the wound and results were expressed as mean percentage wound repair +/−SEM.

Immunofluorescent staining—HUVEC were cultured in basal media with or without TWEAK (200 ng/ml), bFGF (1 ng/ml) or both factors for 24 hours. Cells were detached as described above and stained with $10 \mu g/ml$ primary antibody in 200 $\mu l$ PBS containing 0.1% bovine serum albumin and 0.02% $NaN_3$ for 20 minutes at 4° C. Following washes with the same buffer, the PE-conjugated detection antibodies were added at concentrations as specified by the manufacturer for an additional 15 minutes at 4° C. Cells were analyzed for TWEAK binding by incubation with TWEAK tagged either with flag or with myc. Binding was detected with either biotinylated mouse anti-flag antibody or biotinylated BE.B3 and streptavidin-PE. Cold competition was performed with non-tagged TWEAK and blocking was performed with the AB.D3 mAb.

Capillary tube formation assay—Capillary tube formation by ECs was analyzed using a three-dimensional fibrin matrix gel assay based on a method previously described (Mach, F., et al., 1999. Am. J. Pathol. 154:229–239). Briefly, 4 mg/ml plasminogen free human fibrinogen (Calbiochem, San Diego, Calif.) was dissolved in serum free EBM-2 media with heparin and polymixin B both at 1 ug/ml (Sigma) as well as all of the supplier supplements except for VEGF and bFGF. The fibrin solution was filtered-sterilized and fibrin matrices were prepared by adding thrombin (20–50 milliunits/ml) (Sigma) and distributing 300 ul per well in 24-well plates. ECs at appropriate concentrations ($4\times10^4$ cells/$cm^2$ for HUVEC and HPAEC and $8\times10^4/cm^2$ for HMVEC-L and HMVEC-D) were then seeded onto the gel surfaces and overlayered with EBM-2 media as above and 5% FBS in the presence or absence of TWEAK, bFGF, sCD40L or combinations of these factors as specified. After 72 hours of culture, phase-contrast photomicrographs of the gel surface were taken. Gels were transferred from original wells to new wells and fixed with 10% ethanol for 10 minutes and then with 4% paraformaldehyde. Gels were cross sectioned for analysis and photographs taken.

Example 1

TWEAK Enhances bFGF-dependent Proliferation

Figure 1:
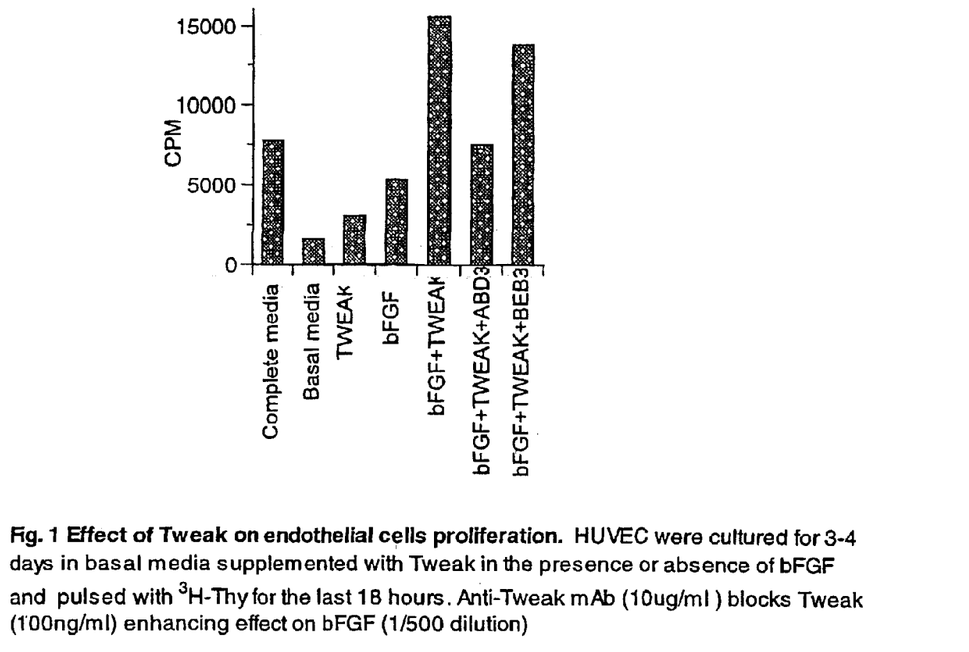
FIG. 1 illustrates the effect of TWEAK on bFGF-dependent HUVEC proliferation.

The effect of TWEAK on EC functions was investigated by examining EC proliferation in cultures treated with TWEAK alone and in combination with another angiogenic growth factors. Human Umbilical Vein EC (HUVEC) were cultured in basal media in the presence or absence of bFGF (FIG. 1). Addition of TWEAK induced no significant proliferation of ECs. By contrast, cells cultured with TWEAK and an optimal concentration of bFGF displayed a significantly enhanced proliferative response compared to cells cultured in the presence of bFGF alone. The degree of proliferation achieved was comparable to or greater than that of ECs cultured in complete media Similar results were obtained using bFGF at 1 ng/ml. The synergistic activity of TWEAK with bFGF was completely inhibited by anti-TWEAK mab AB.D3 suggesting that the effect of TWEAK was specific, whereas there was no inhibition by a anti-TWEAK mAb BE.B3 or an irrelevant control Ig. In addition, no enhancement was seen with recombinant soluble APRIL, another TNF ligand (data not shown). The experimental conditions for the results shown in FIG. 1 are described here in detail. HUVEC were cultured in complete media or in basal media. TWEAK (100 ng/ml), bFGF (1/500 dilution) or combinations of these factors were added to basal media as indicated for 3 days and proliferation measured by $^3$H-thymidine incorporation. In FIG. 1, data shown are the mean value +/−SD of triplicate wells. These results are representative of 4 independent experiments wherein proliferation in bFGF+TWEAK-treated cultures was significantly different from that of cultures with bFGF alone, TWEAK alone and basal media (P values <0.05), and the difference between cultures in basal media with and without TWEAK was not significant. In addition to growth factors, blocking anti-TWEAKmAb AB.D3, nonblocking anti-TWEAK mAb BE.B3, and an irrelevant hamster control Ig Ha4/8 (10 ug/ml) were added where indicated. Results are representative of one of two independent experiments.

Example 2

Figure 2:
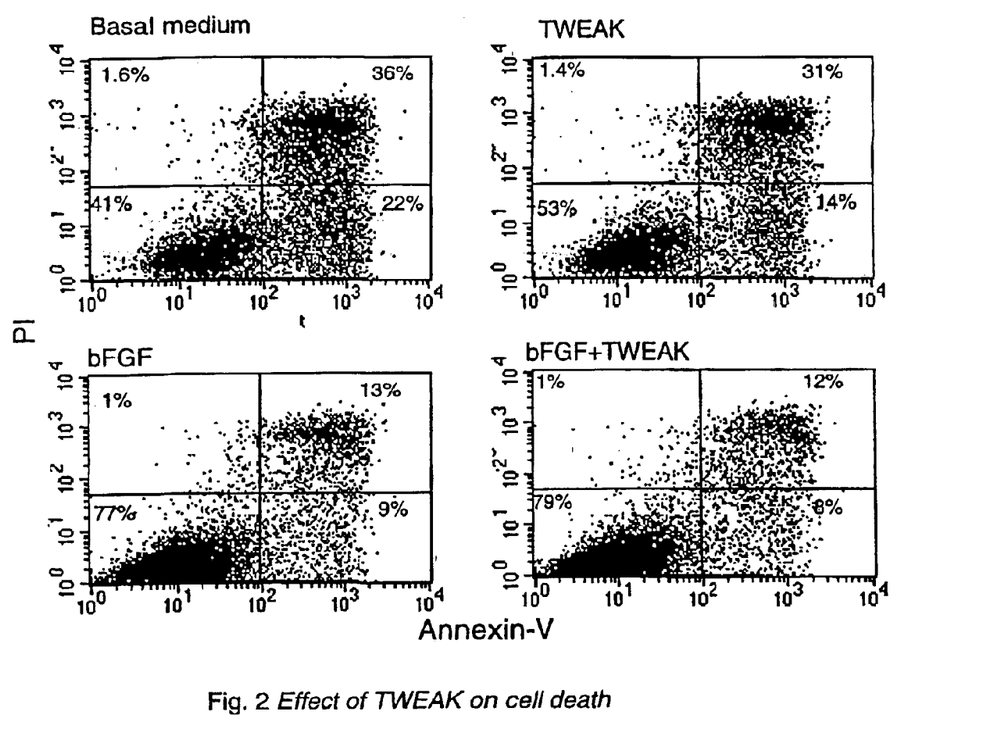
FIG. 2 illustrates the effect of TWEAK on HUVEC death.

Enhancement of EC Proliferation by TWEAK with bFGF is not Due to Decreased Cell Death The apparent enhancement of HUVEC proliferation by the TWEAK/bFGF combination could be due to increased cell division or decreased cell death. In order to address the mechanism, HUVEC cultured in basal media with or without TWEAK, bFGF or both were analyzed to determine the frequency of apoptotic cells. Annexin V staining was employed to detect cells undergoing apoptosis and propidium iodide (PI) dye exclusion to detect viable cells. Cultures treated with the combination of TWEAK and bFGF exhibited percentages of viable, apoptotic and dead cells that were comparable to those of cultures treated with bFGF alone. These percentages are shown in FIG. 2, in quadrants 3, 4 and 2 respectively. Similar results were obtained in two additional experiments wherein cells with subdiploid DNA content were quantified (11% in bFGF and 11% in bFGF/TWEAK treated cultures). Thus, the enhancement by TWEAK of bFGF-dependent proliferation is not due to decreased cell death. Nevertheless it is noteworthy that TWEAK alone decreased the frequency of apoptotic cells from 22% to 14%. This pattern also was observed in two independent experiments, wherein the percentage of cells with subdiploid DNA were on average 18+/−1% and 9+/−0% in the absence and presence of TWEAK, respectively.

The experimental conditions for the results in FIG. 2 are described in detail here. HUVEC cultured for 24 hours in basal media with or without TWEAK (200 ng/ml), bFGF (1 ng/ml) or both cytolines were stained with FITC-Annexin-V (x-axis) for apoptotic cells and by PI dye exclusion for viability (y-axis). FIG. 2 shows the percentage of viable, apoptotic and dead cells in quadrants 3, 4, and 2, respectively.

Example 3

TWEAK Enhances bFGF-dependent HUVEC Migration

The ability of TWEAK to effect EC migration was evaluated in the presence and absence of other angiogenic factors. Confluent HUVEC monolayers were wounded and EC migration was monitored within the first 18 hours by determining the degree of wound repair. Addition of TWEAK or bFGF to basal media induced a low level of wound repair, however, this was not significantly greater than that observed with basal media alone. By contrast, cultures treated with both TWEAK and bFGF were repaired to a significantly greater degree than cultures in basal media and with either agent alone, and were similar to those in complete media HUVECs were recovered from the cultures and counted in order to determine whether or not any increase in cell number had occurred over the course of the experiment. In all treatment groups, cell recoveries were comparable (data not shown) supporting that the combinatorial effect of TWEAK and bFGF was at the level of cell migration.

Figure 3:
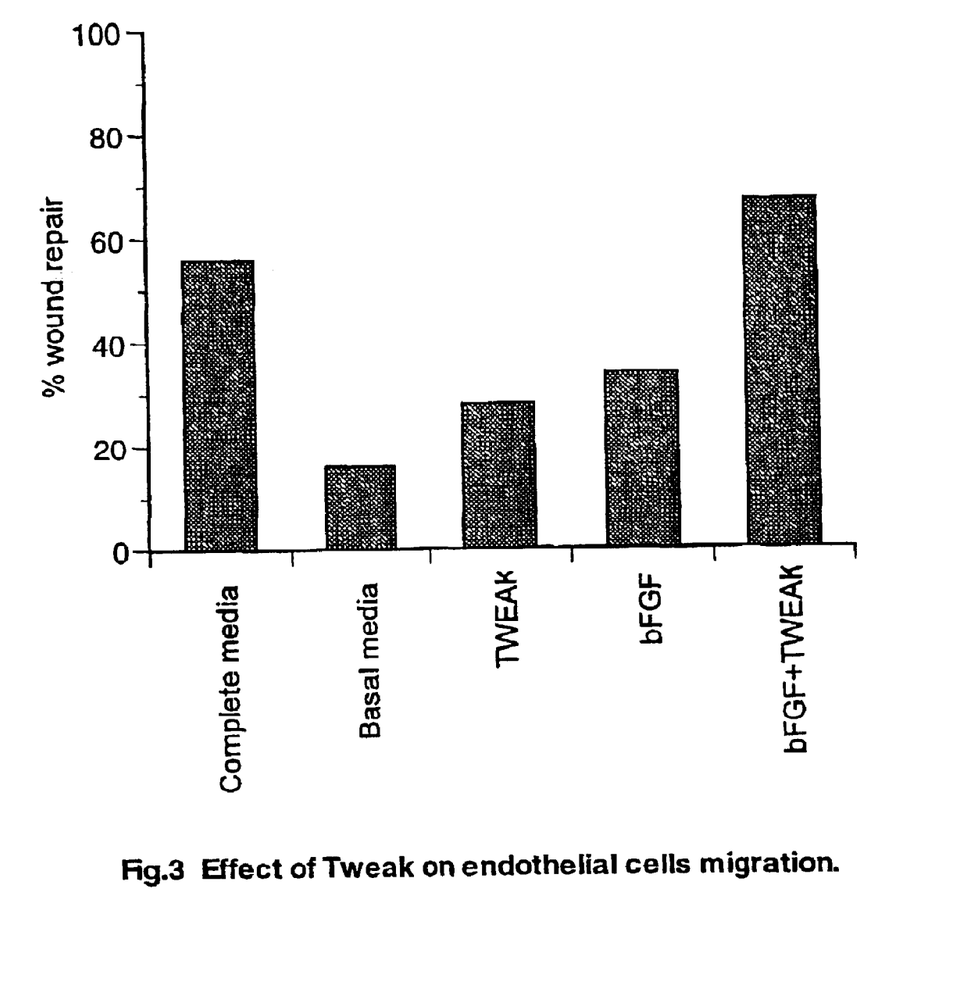
FIG. 3 illustrates the effect of TWEAK on bFGF-dependent HUVEC migration.

The experimental conditions for the results shown in FIG. 3 are described here in detail. Confluent HUVEC monolayers treated with TWEAK (200 ng/ml), bFGF (1 ng/ml or 1/1000 dilution), and combinations of these factors, were wounded and repair measured after 18 hours of culture. FIG. 3 shows the average of 4 experiments +/−SEM, with repair induced by bFGF+TWEAK significantly different from that induced by either alone or basal media (P values <0.05).

Example 4

Effect of TWEAK is not Mediated by Modulation of Growth Factor Receptors or Integrins Integrins, especially $\alpha_v\beta_3$, $\alpha_1\beta_1$ and $\alpha_2\beta_1$ facilitate cell migration through extracellular matrix and also regulate cell survival and intracellular signaling required for the response to angiogenic factors (Eliceiri, B. and Cheresh, D. A., 1999. J.Clin. Invest.103:1227–1230; Senger, D. R., et al., 1997. Proc. Natl. Acad. Sci 94:13612–13617). Therefore, we aimed to determine whether or not TWEAK modulated growth factor receptors or integrins expressed on ECs. VEGF receptors Flk-1 and Flt-1 and bFGF receptor Flg were expressed at very low levels on HUVECs cultured in basal media. As a positive control, these receptor-specific mAbs showed strong staining on human dermal microvascular EC (HMVEC-D). Consistent with the study by Lynch et al (11), we found no change in the expression of VEGF receptors Flk-1 and Flt-1 in TWEAK treated cultures, nor were there changes in VEGF receptor expression in cultures treated with bFGF or the TWEAK/bFGF combination. In addition, we found that TWEAK treatment did not alter the level of the bFGF receptor Flg or of integrins $\alpha_v$, $\alpha_1$, $\alpha_5$, $\beta_1$, and $\beta_3$.

Example 5

TWEAK Induces EC Morphogenesis

Figure 4:
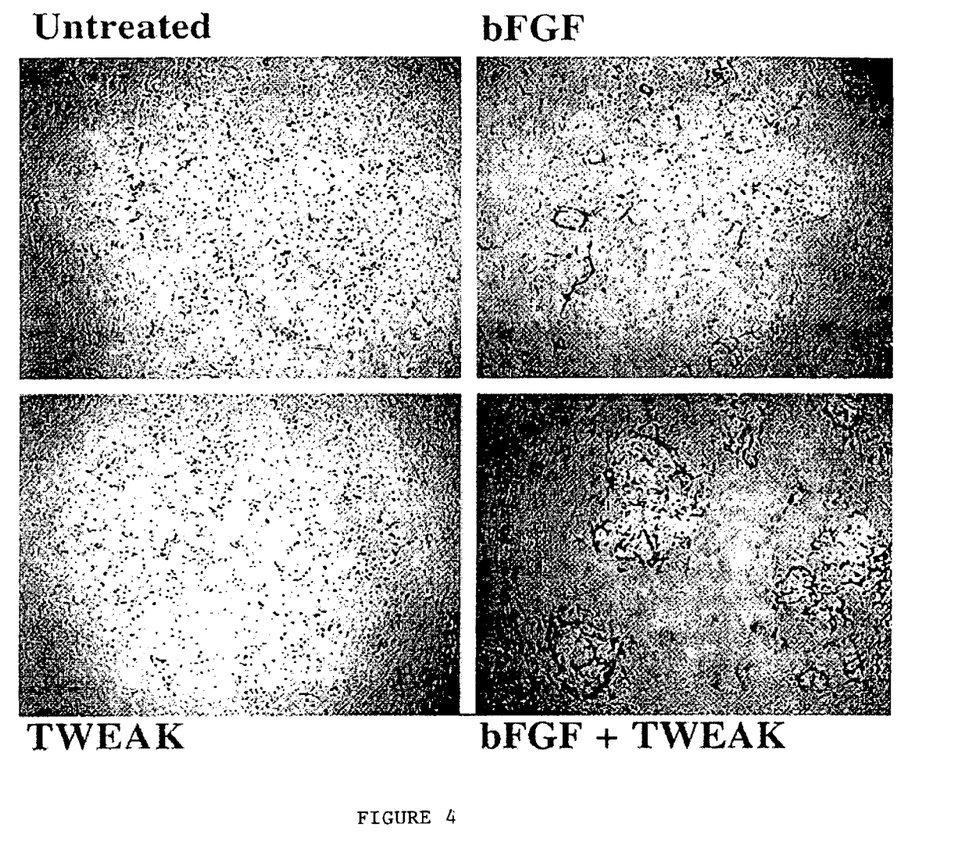
FIG. 4 depicts the synergistic effect of TWEAK and bFGF on capillary tube formation.

A key event in the angiogenic process is the organization of invading ECs into capillary tubes. The effect of TWEAK on this morphogenic step was measured with EC seeded onto the surface of three-dimensional fibrin gels in the presence or absence of bFGF. We found no effect of TWEAK on the EC monolayer, while an optimal concentration of bFGF promoted cell invasion and organization of EC into cords. The addition of TWEAK to bFGF induced clear morphological changes in the EC monolayer. Similar results were obtained with several different EC types, including HUVECs, human pulmonary artery ECs (HPAEC), human lung microvascular EC (HMVEC-L)and HMVEC-D. In addition, cross-sectional analysis of these gels revealed that the addition of TWEAK to bFGF induced the structural organization of invading ECs into tubes with lumens. CD40L, another TNF member, had no effect wither alone or in combination with bFGF. Thus TWEAK synergizes with bFGF to induce the morphogenesis of capillary lumens. The results are shown in FIG. 4.

We claim:

1. A method for enhancing endothelial cell proliferation in an in vitro culture comprising the step of adding to said culture, a synergistically effective amount of TWEAK and basic fibroblast growth factor (bFGF).

2. A method for enhancing angiogenic activity in a mammal to promote neovascularization comprising the step of administering to said mammal a synergistically effective amount of TWEAK and basic fibroblast growth factor (bFGF).

3. The method according to claim 2, wherein said method is used in the treatment of a myocardial ischemic condition in said mammal.

4. The method according to claim 2, wherein said method is used to promote wound healing in said mammal.

5. The method according to claim 1 or 2, wherein said TWEAK is a soluble recombinant TWEAK protein.

6. The method according to claim 1 or 2, wherein said synergistically effective amount comprises basic fibroblast growth factor (bFGF) and TWEAK in a weight per weight ratio of at least about 1:100 to about 1:200.

7. The method according to claim 2, wherein said method is used to promote neovascularization of transplanted or grafted tissues or organs in said mammal.

8. The method according to any one of claims 2, 3, 4 or 7, wherein said mammal is a human.

9. The method according to any one of claims 2, 3, 4 or 7, wherein said TWEAK and said basic fibroblast growth factor (bFGF) are administered by a route selected from the group consisting of: local injection, topical administration, parenteral administration, intranasal administration, intratracheal administration, pulmonary administration, oral administration, intravenous administration, intramuscular administration and subcutaneous administration.

* * * * *